US009114092B2

(12) United States Patent
Lee et al.

(10) Patent No.: US 9,114,092 B2
(45) Date of Patent: Aug. 25, 2015

(54) NANOTOPOGRAPHY-MEDIATED REVERSE UPTAKE PLATFORM FOR NUCLEIC ACID DELIVERY AND APPLICATIONS THEREOF

(71) Applicant: Rutgers, The State University of New Jersey, New Brunswick, NJ (US)

(72) Inventors: Ki-Bum Lee, Monmouth Junction, NJ (US); Aniruddh Solanki, South Plainfield, NJ (US); Shreyas Shah, Dayton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/751,690

(22) Filed: Jan. 28, 2013

(65) Prior Publication Data

US 2013/0236552 A1    Sep. 12, 2013

Related U.S. Application Data

(60) Provisional application No. 61/591,303, filed on Jan. 27, 2012.

(51) Int. Cl.
| | |
|---|---|
| *C07H 21/04* | (2006.01) |
| *A61K 9/51* | (2006.01) |
| *A61K 31/713* | (2006.01) |
| *C12N 15/11* | (2006.01) |
| *C12N 15/113* | (2010.01) |

(52) U.S. Cl.
CPC .............. *A61K 9/51* (2013.01); *A61K 31/713* (2013.01); *C12N 15/111* (2013.01); *C12N 15/113* (2013.01); *C12N 2310/14* (2013.01); *C12N 2320/32* (2013.01)

(58) Field of Classification Search
CPC ............... C12N 15/111; C12N 15/113; C12N 2310/14; A61K 9/51
See application file for complete search history.

(56) References Cited

U.S. PATENT DOCUMENTS

| | | | | |
|---|---|---|---|---|
| 7,829,140 | B1 * | 11/2010 | Zhong et al. ................ | 427/212 |
| 2006/0159916 | A1 * | 7/2006 | Dubrow et al. ............. | 428/357 |
| 2007/0014773 | A1 * | 1/2007 | Matheny et al. ........... | 424/93.21 |
| 2009/0233074 | A1 * | 9/2009 | Haynie ........................ | 428/220 |
| 2010/0028453 | A1 * | 2/2010 | Yoo et al. .................... | 424/497 |
| 2010/0221836 | A1 * | 9/2010 | Rickus et al. ............... | 435/404 |
| 2011/0189287 | A1 * | 8/2011 | Abbott et al. ............... | 424/484 |
| 2012/0094382 | A1 * | 4/2012 | Park et al. ................... | 435/372.2 |
| 2012/0323112 | A1 * | 12/2012 | Jokerst et al. .............. | 600/420 |
| 2013/0244889 | A1 * | 9/2013 | Yim et al. .................... | 506/7 |

OTHER PUBLICATIONS

Adler et al., "Emerging links between surface nanotechnology and endocytosis: impact on nonviral gene delivery," Nano Today, (2010) vol. 5, pp. 553-569.
Beebe et al., "Nanosecond, high-intensity pulsed electric fields induce apoptosis in human cells," Faseb J. (2003) vol. 17, pp. 1493-1495.
Biggs et al., "Nanotopographical modification: a regulator of cellular function through focal adhesions," Nanomedicine., (2010) vol. 6, pp. 619-633.
Cavalcanti-Adam et al., "Cell Spreading and Focal Adhesion Dynamics Are Regulated by Spacing of Integrin Ligands," Biophys. J, (2007) vol. 92, pp. 2964-2974.
Dalby et al., "Use of nanotopography to study mechanotransduction in fibroblasts—methods and perspectives," Eur. J Cell Biol. (2004) vol. 83, pp. 159-169 (Abstract only).
Guilak et al., "Control of stem cell fate by physical interactions with the extracellular matrix," Cell Stem Cell (2009) vol. 5, 17-26.
Hoelters et al., "Nonviral genetic modification mediates effective transgene expression and functional RNA interference in human mesenchymal stem cells," J. Gene Med, (2005) vol. 7, pp. 718-728 (Abstract only).
Kim et al., "Synergistic induction of apoptosis in brain cancer cells by targeted codelivery of siRNA and anticancer drugs," Mol. Pharm. (2011) vol. 8, pp. 1955-1961.
Shalek et al., "Vertical silicon nanowires as a universal platform for delivering biomolecules into living cells," Proc. Natl. Acad Sci. USA, (2010) vol. 107, pp. 1870-1875.
Shi et al., "Caveolin-1-dependent ?1 integrin endocytosis is a critical regulator of fibronectin turnover," J Cell Sci., (2008) vol. 121, pp. 2360-2371.
Solanki et al., "Controlling Differentiation of Neural Stem Cells Using Extracellular Matrix Protein Patterns," Small, (2010) vol. 6, pp. 2509-2513.
Yoo, et al., "Bio-inspired, bioengineered and biomimetic drug delivery carriers," Nat. Rev. Drug Discov. (2011) vol. 10, pp. 521-535 (Abstract only).
Zhang et al., "SiRNA-loaded multi-shell nanoparticles incorporated into a multilayered film as a reservoir for gene silencing," Biomaterials, (2010) vol. 31, pp. 6013-6018 (Abstract only).

* cited by examiner

*Primary Examiner* — Brian Whiteman
(74) *Attorney, Agent, or Firm* — Fox Rothschild LLP

(57) ABSTRACT

This application discloses a nanotopography-mediated reverse uptake (NanoRU) platform useful for intracellular delivery of nucleic acids into mammalian cells, in particular stem cells, as well as methods of preparation and applications thereof. In particular, this system can be used to deliver small interfering ribonucleic acids (siRNAs) into neural stem cells and enhance neuronal differentiation of the stem cells.

12 Claims, 8 Drawing Sheets

SEQUENCE LISTING

<160> NUMBER OF SEQ ID NOS: 16

<210> SEQ ID NO 1
<211> LENGTH: 21
<212> TYPE: RNA
<213> ORGANISM: Artificial
<220> FEATURE:
<223> OTHER INFORMATION: Synthetic GFP siRNA Antisense

<400> SEQUENCE: 1
ccaacgacau cagcgacuau u                                              21

<210> SEQ ID NO 2
<211> LENGTH: 21
<212> TYPE: RNA
<213> ORGANISM: Artificial
<220> FEATURE:
<223> OTHER INFORMATION: GFP siRNA Sense

<400> SEQUENCE: 2
uugguugcug uagucgcuga u                                              21

<210> SEQ ID NO 3
<211> LENGTH: 21
<212> TYPE: RNA
<213> ORGANISM: Artificial
<220> FEATURE:
<223> OTHER INFORMATION: Synthetic SOX9 siRNA Antisense

<400> SEQUENCE: 3
aacgagagcg agaagagacc c                                              21

<210> SEQ ID NO 4
<211> LENGTH: 21
<212> TYPE: RNA
<213> ORGANISM: Artificial
<220> FEATURE:
<223> OTHER INFORMATION: Synthetic SOX9 siRNA Sense

<400> SEQUENCE: 4
uugcucucgc ucuucucugg g                                              21

<210> SEQ ID NO 5
<211> LENGTH: 20
<212> TYPE: DNA
<213> ORGANISM: Artificial
<220> FEATURE:
<223> OTHER INFORMATION: Synthetic FAK primer

<400> SEQUENCE: 5
caatgcctcc aaattgtcct                                                20

<210> SEQ ID NO 6
<211> LENGTH: 20
<212> TYPE: DNA
<213> ORGANISM: Artificial
<220> FEATURE:
<223> OTHER INFORMATION: Synthetic FAK reverse primer

<400> SEQUENCE: 6
tccatcctca tccgttcttc                                                20

<210> SEQ ID NO 7
<211> LENGTH: 20
<212> TYPE: DNA
<213> ORGANISM: Artificial

```
<220> FEATURE:
<223> OTHER INFORMATION: Synthetic GAPDH primer

<400> SEQUENCE: 7
atgactctac ccacggcaag                                              20

<210> SEQ ID NO 8
<211> LENGTH: 20
<212> TYPE: DNA
<213> ORGANISM: Artificial
<220> FEATURE:
<223> OTHER INFORMATION: Synthetic GAPDH reverse primer

<400> SEQUENCE: 8
ggaagatggt gatgggtttc                                              20

<210> SEQ ID NO 9
<211> LENGTH: 21
<212> TYPE: DNA
<213> ORGANISM: Artificial
<220> FEATURE:
<223> OTHER INFORMATION: Synthetic GFAP primer

<400> SEQUENCE: 9
gagagagatt cgcactcagt a                                            21

<210> SEQ ID NO 10
<211> LENGTH: 20
<212> TYPE: DNA
<213> ORGANISM: Artificial
<220> FEATURE:
<223> OTHER INFORMATION: Synthetic GFAP reverse primer

<400> SEQUENCE: 10
tgaggtctgc aaacttggac                                              20

<210> SEQ ID NO 11
<211> LENGTH: 21
<212> TYPE: DNA
<213> ORGANISM: Artificial
<220> FEATURE:
<223> OTHER INFORMATION: Synthetic MBP primer

<400> SEQUENCE: 11
cacaagaact acccactacg g                                            21

<210> SEQ ID NO 12
<211> LENGTH: 20
<212> TYPE: DNA
<213> ORGANISM: Artificial
<220> FEATURE:
<223> OTHER INFORMATION: Synthetic MBP reverse primer

<400> SEQUENCE: 12
gggtgtacga ggtgtcacaa                                              20

<210> SEQ ID NO 13
<211> LENGTH: 22
<212> TYPE: DNA
<213> ORGANISM: Artificial
<220> FEATURE:
<223> OTHER INFORMATION: Synthetic SOX9 primer

<400> SEQUENCE: 13
aggaagctgg cagaccagta cc                                           22
```

```
<210> SEQ ID NO 14
<211> LENGTH: 20
<212> TYPE: DNA
<213> ORGANISM: Artificial
<220> FEATURE:
<223> OTHER INFORMATION: Synthetic SOX9 reverse primer

<400> SEQUENCE: 14
tctcttctcg ctctcgttca                                          20

<210> SEQ ID NO 15
<211> LENGTH: 21
<212> TYPE: DNA
<213> ORGANISM: Artificial
<220> FEATURE:
<223> OTHER INFORMATION: Synthetic TUJ1 primer

<400> SEQUENCE: 15
actttatctt cggtcagagt g                                        21

<210> SEQ ID NO 16
<211> LENGTH: 20
<212> TYPE: DNA
<213> ORGANISM: Artificial
<220> FEATURE:
<223> OTHER INFORMATION: Synthetic TUJ1 reverse primer

<400> SEQUENCE: 16
ctcacgacat ccaggactga                                          20
```

NANOTOPOGRAPHY-MEDIATED REVERSE UPTAKE PLATFORM FOR NUCLEIC ACID DELIVERY AND APPLICATIONS THEREOF

CROSS-REFERENCE TO RELATED APPLICATIONS

This application claims priority under 35 U.S.C. §119(e) to U.S. Provisional Patent Application Ser. No. 61/591,303, filed on Jan. 27, 2012, which is hereby incorporated by reference in its entirety.

STATEMENT REGARDING FEDERALLY SPONSORED RESEARCH

The invention described herein was supported in whole or in part by grants from the National Institutes of Health (New Innovator Award No. NIH-IDP20D00646201). The U.S. Government has certain rights in this invention.

FIELD OF THE INVENTION

The present invention relates to a nanotopography-mediated reverse uptake platform for intracellular delivery of nucleic acids, in particular small interfering RNA (siRNA), into stem cells and applications thereof.

BACKGROUND OF THE INVENTION

In the last decade, various methods have been developed to deliver genetic material into stem cells thr the specific control of gene expression. The most common methods include solution-based delivery using viruses, non-viral cationic lipids, nanoparticles, and polyplexes (see, e.g., Kim. C., et al., *Mol. Pharm.* 8, 1955-1961 (2011)). However, when treated with exogeneous materials, stem cells tend to die or undergo undesired differentiation patterns. Therefore, there are concerns associated with the introduction of viruses, nanoparticles, and other exogenous materials into stem cells (Yoo, J. W., et al., *Nat Rev. Drug Discov.* 10, 521-535 (2011)). Another commonly used technique, which circumvents this issue, is electroporation (Hoelters, J., et al. *J. Gene Med.* 7, 718-728 (2005)). However, electroporation has been shown to cause high levels of cell death due to physical damage to the cell membrane in addition to the introduction of other undesired materials into the cell (e.g. ions, which can shill the concentration gradient) (Beebe, S. J., et al., *Faseb J.* 17, 1493-1495 (2003)). Therefore, the development of new methods to safely and effectively deliver genetic materials into stem cells is needed.

Recently, increasing attention has been given to substrate-mediated genetic delivery, in which cells uptake biomaterials from the substrate on which they are grown. These methods can potentially facilitate the uptake of genetic material in a noninvasive fashion and prevent the need to deliver exogenous materials. Shalek et al. reported that silicon nanowires, which physically impale cells, can deliver genes and siRNA (Shalek, A. K., et al., *Proc. Natl. Acad. Sci. USA* 107, 1870-1875 (2010)). This system has been shown to be very efficient at delivering genetic material into a variety of cell types, including stem cells. Nevertheless, the mechanism governing how nanowires affect cell physiology remains to be investigated. Reverse transfection, or the substrate-mediated uptake, of siRNA by cells has also been explored using the layer-by-layer technique (Zhang, X., et al., *Biomaterials* 31, 6013-6018 (2010)). However, such techniques require the use of cationic polymers, similar to the ones used in solution-based transfection, which may not be ideal in terms of maintaining stem cell viability. Therefore, there is a pressing need to further develop and characterize substrate-mediated strategies that can facilitate nucleic acid delivery into stem cells. These techniques are of particular importance for investigating and controlling differentiation.

The stem cell microenvironment plays a major role in controlling various stem cell behaviors. It has already been demonstrated that stem cell fate can be controlled by making ECM protein patterns of different geometries and dimensions (Solanki, A., et al., *Small* 6, 2509-2513 (2010); Guilak, F., et al., *Cell Stem Cell* 5, 17-26 (2009)). While stem cell differentiation can be controlled by manipulating the expression of certain genes, it remains a question whether topographical features of the ECM can be utilized to control this expression.

One of the critical barriers to harnessing the full therapeutic potential of stem cells is the development of an easy, effective, and non-toxic methodology to control differentiation into specific cell lineages. Stem cell differentiation can be controlled by modulating key gene expression levels or signaling pathways within the cell, which has been achieved by several conventional gene delivery methods. For example, the RNA interference (RNAi) method. For controlling gene expression levels using siRNA or miRNA is emerging as an important tool in stem cell biology. For the successful genetic manipulation of stem cells, the cells must typically maintain their viability for an extended period of time after single or multiple siRNA transfections, without affecting the intrinsic cellular functions. However, many of the conventional methods used to deliver siRNA into stem cells, including lipid-based transfections, viral vectors, nanowire-based platforms, and electroporation techniques, result in significant cytotoxicity and undesirable side-effects. This presents a considerable challenge for the development of both, robust and reliable siRNA delivery into stem cells to control their differentiation into the desired cell lineages.

Currently, one of the most common methods to deliver siRNA into stem cells is the solution-mediated delivery (or forward transfection) using exogenous chemical materials including non-viral cationic lipids, nanoparticles, and polymers. However, such exogenous materials may be cytotoxic for the delivery of siRNA into stem cells and thereby need to be removed after a certain incubation period. In addition, they can potentially compromise the ability of stem cells to proliferate, migrate and differentiate. Therefore, there are several limitations associated with the solution-mediated delivery methods for manipulating gene expression within stem cells. In order to address these limitations, increasing attention has been given to the substrate-mediated delivery of siRNA, wherein the cells directly uptake the siRNA from the underlying substrate. Substrate-mediated delivery can potentially facilitate the uptake of siRNA into stem cells, which precludes the need to use exogenous materials as delivery vehicles. For instance, it was reported that silicon nanowires, which physically impale the cell membrane, can deliver siRNA into the cellular cytoplasm. Nevertheless, the potential physical damage caused by the nanowires on the plasma membranes of cells and the mechanism of how the nanowire arrays transfer siRNA into cells was not addressed. Moreover, the survival of stem cells for extended periods, which is required for their differentiation, was not demonstrated. Thus, there is a clear need to develop nontoxic, and efficient strategies to deliver siRNA into stem cells to control gene expression levels, such that we can maintain the biological functions of stem cells for extended periods of time and efficiently control their differentiation into specific cell types.

SUMMARY OF THE INVENTION

The present invention is a response to the foregoing need by providing a nanotopography-mediated reverse uptake platform (NanoRU) for delivering siRNA into neural stem cells (NSCs) in a non-toxic and highly effective manner using nanoparticle-based topographical structures.

In one aspect the present invention provides a nucleic acid delivery system comprising a self-assembled silicon oxide (silica) nanoparticle (SiNP) monolayer coated with a film comprising one or more of extracellular matrix (ECM) proteins, the film having topographical features capable of facilitating delivery of a nucleic acid into cells.

In another aspect the present invention provides a method of controlling differentiation of stem cells, comprising delivering a nucleic acid into the stem cells using the nucleic acid delivery system as described above.

In another aspect the present invention provides a method of enhancing neuronal differentiation of neural stem cells comprising nanotopography-mediated delivery of siRNA or genes into the neural stem cells using a nucleic acid delivery platform as described above.

In another aspect the present invention provides a gene therapy for treating a disease or disorder, comprising administering to a patient in need thereof stem cells that have undergone controlled differentiation as described above.

In another aspect, the present invention provides a nucleic acid delivery kit comprising a nucleic acid delivery platform as described above.

In another aspect the present invention provides a method of preparing a nucleic acid delivery platform as described above, comprising the steps of: (1) providing a glass substrate; (2) coating the glass substrate with a thin film of gold; (3) forming self assembled monolayer(s) (SAMs) of a negatively charged bifunctional organic compound on the gold film; (4) generating a silica nanoparticle (SiNP) film on the coated gold film; and (5) coating the SiNP film with one or more ECM protein(s).

From the vast repertoire of techniques that can be used to deliver siRNA into stem cells, methods based on substrate-mediated delivery, where cells uptake siRNA from their microenvironments, are extremely advantageous as they provide a way to improve the efficiency of siRNA delivery by simply changing the cellular microenvironment. However, until the present invention. Whether nanotopographical features of the extracellular microenvironment can be used to efficiently deliver siRNA into stem cells and the effects that the topographical features of the extracellular microenvironment (ECM) have on siRNA uptake by the stem cells remained to be explore. Herein, we have developed a nanotopography-mediated delivery platform (NanoRU) to demonstrated a simple technique to deliver siRNA into neural stem cells (NSCs), using positively charged nanoparticle films that are coated with an ECM protein, such as laminin, and the desired siRNA. NanoRU consists of a self-assembled silica nanoparticle (SiNP) monolayer coated with extracellular matrix (ECM) proteins and the desired siRNA. We showed that siRNA delivery to NSCs is dependent on the size of the nanoparticles and that only the siRNA molecules, not the nanoparticles, are taken up by the NSCs. Furthermore, we exemplified this technique to efficiently deliver siRNA against the transcription factor SOX9, which acts as a switch between the neuronal and glial fate of NSCs. The knockdown of SOX9 enhanced the neuronal differentiation and decreased the glial differentiation of the NSCs. The present invention demonstrates the ease of application and the importance of nanotopography-mediated siRNA delivery into stem cells as an effective method for genetic manipulation.

The present invention demonstrates a highly efficient nanotopography-mediated delivery of siRNA molecules into neural stem cells (NSCs) cultured on films of positively charged silicon oxide nanoparticles coated with an ECM protein such as laminin. In one embodiment, the siRNA molecules specifically knockdown the transcription factor SOX9, which results in a significant increase in the neuronal differentiation of NSCs. This novel approach does not require the use of cationic transfection agents which are typically used for siRNA delivery. The positively charged SiNP films are coated with negatively charged siRNA and the ECM protein. Thus, without intent to be bound by any theory, the method of the present invention relies upon uptake of siRNA by stem cells based upon the nanotopographical features of the underlying surface.

Delivering siRNA into stem cells is very challenging and the existing popular methods of siRNA delivery cause cell death or involve the use of viruses which is not particularly appealing. The present invention provides a useful alternative for scientists to deliver siRNA and genes into stem cells. The method is straight-forward and does not require the use of viruses or materials which could cause cell death. Another important aspect of the present invention is that the NSCs take up only the siRNA/DNA and not the nanoparticles from the surface. The nanoparticles are tightly bound to the underlying substrate, and it is advantageous that the NSCs (or other cells) take up only the siRNA/DNA from the surface but not the nanoparticles, since there would be no concerns regarding the toxicity of nanoparticles.

These and other aspects of the present invention will be better appreciated in view of the following drawings, detailed descriptions, and claims.

DETAILED DESCRIPTION OF THE INVENTION

Figure 1:
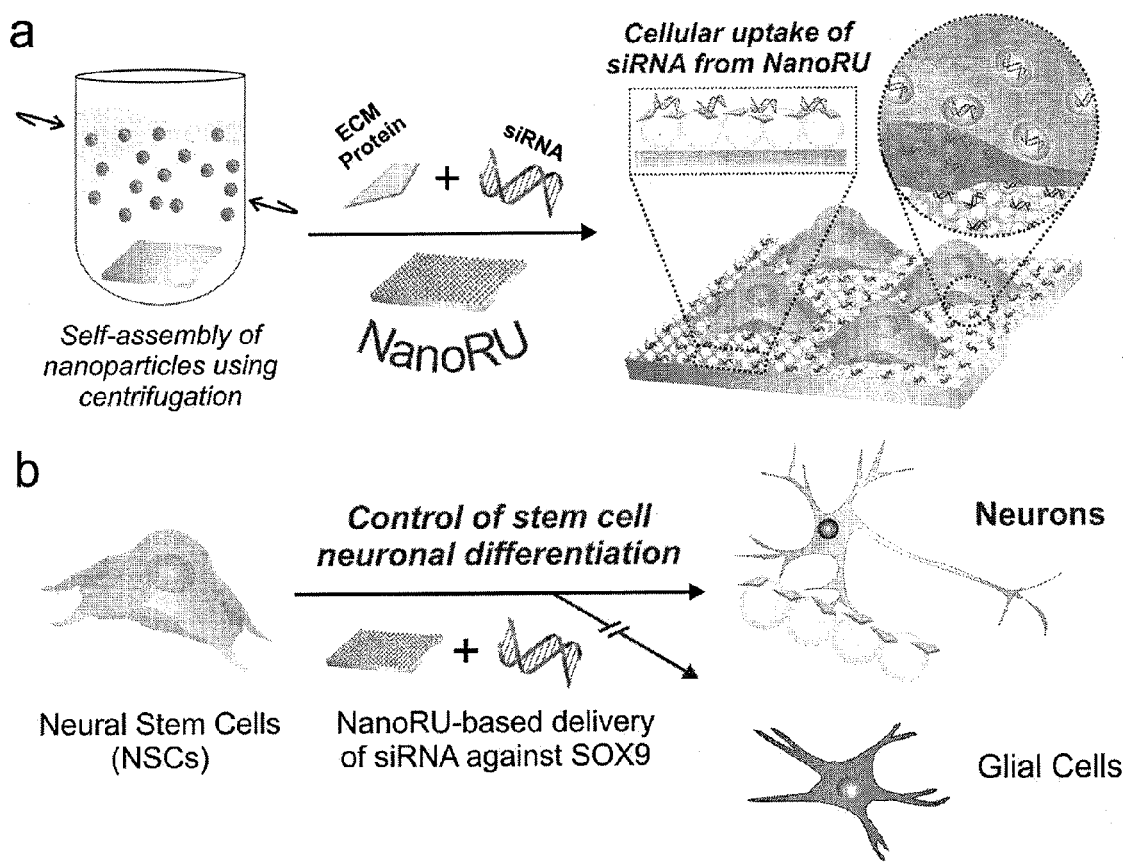
FIG. 1 illustrates a schematic diagram of reverse uptake for siRNA delivery into stem cells from nanoparticle films.

In an effort to address the aforementioned challenges, the present invention provides a nanotopography-mediated reverse uptake platform (NanoRU) for delivering siRNA into neural stem cells (NSCs), in a non-toxic and highly effective manner using nanoparticle-based topographical structures. NanoRU was fabricated by assembling monodisperse nanoparticles on a glass substrate using centrifugation. Moreover, the size of nanoparticles was used to generate differences in nanotopography within the microenvironment (FIG. 1). As a proof-of-concept, we studied the interaction of NSCs with different sizes of nanoparticles; a parameter we believe plays a critical, role in the uptake of siRNA by the NSCs. Since NSCs have been known to be highly sensitive to nanotopographical and physical cues, we identified the optimal size of nanoparticles, which facilitated the highest uptake of siRNA by the NSCs. To accomplish this, we assessed the efficiency of RNAi by examining the suppression of green fluorescent protein (GFP) in NSCs which were genetically modified to express GFP. Based on the GFP knockdown, we then utilized the optimized NanoRU to specifically knockdown the neural switch gene, SOX9, which resulted in significantly enhanced neuronal differentiation of NSCs. Thus, NanoRU relies upon the nanotopographical features of the extracellular microenvironment to deliver siRNA into NSCs, without using exogenous delivery vehicles. In particular, this novel siRNA delivery approach does not require the use of lipid-based cationic transfection agents, which are generally cytotoxic to stem cells.

While not being limited to any particular theory, in accordance with the present invention it has been discovered that nanotopography-mediated siRNA and gene delivery (without the use of cationic lipids or polymers) can be achieved by using extracellular matrix protein, such as laminin, which has a negative charge. The varying nanotopographical features were created by making films of positively charged (amine-terminated) silicon oxide nanoparticles of varying sizes, including 50 nm, 100 nm, 300 nm, 500 nm, and 700 nm, can be obtained commercially (Corpuscular Inc.) or synthesized by methods known in the art. The films were then coated with a negatively charged ECM protein such as laminin, and siRNA or DNA, which are also negatively charged. They condensed well on the positively charged nanoparticle films. Neural stem cells (NSCs) were first grown on them and as a proof-of-concept, we used green fluorescent protein (GFP) labeled NSCs to efficiently knock down the expression of GFP using this method of delivery. In this way, the NSCs uptake the siRNA (against GFP) from the nanoparticle films. The knockdown was size-dependent, with the 100 nm particle films showing the highest knock down and the 700 nm particle films showing the lowest knock down. However, when nanoparticles below 100 am were used, the efficiency of knockdown was reduced drastically and no change in GFP expression was observed. Thus, it was demonstrated that the invention was workable using the knockdown of GFP as a model system, although the invention is not limited to, and does not require, GFP.

To exemplify in more detail, we generated the SiNP films on glass substrates coated with a thin film (12 nm) of gold. To this end, self-assembled monolayers (SAMs) of negatively charged 16-mercaptohexadecanoic acid (MHA) were first formed on the gold film, followed by centrifugation in a solution of positively charged SiNPs (See methods sections for details). To study the uptake and subsequent knockdown of gene expression by the siRNA in NSCs grown on the SiNP films, we used rat NSCs labeled with human mulleri green fluorescent protein (hmGFP) for these experiments.

Thus, in one aspect the present invention provides a nucleic acid delivery system comprising a self-assembled silicon oxide (silica) nanoparticle (SiNP) monolayer coated with a film comprising one or more of extracellular matrix (ECM) proteins, the film having topographical features capable of facilitating delivery of a nucleic acid into cells.

In one embodiment of this aspect, the silica nanoparticles (SiNPs) are assembled on a thin film of gold coated with a self-assembled monolayer (SAM) of a bifunctional organic compound.

In another embodiment of this aspect, the bifunctional organic compound comprises a thiol (—SH) end group and a carboxylic acid (—COOH) end group.

In another embodiment of this aspect, the ECM proteins are independently selected from the group consisting of laminin, fibronectin, collagen, and combinations thereof.

In a preferred embodiment of this aspect, the ECM protein is laminin.

In another embodiment of this aspect, the sizes of silica nanoparticles are in the range of 50 nm to 700 nm.

In another embodiment of this aspect, the sizes of silica nanoparticles are in the range of 1.00 nm to 300 nm.

In another embodiment of this aspect, the nucleic acid is a small interfering ribonucleic acid (siRNA).

In another embodiment of this aspect, the cells are mammalian cells.

In another embodiment of this aspect, the cells are astrocytes or cancer cells, for example, brain cancer cells and breast cancer cells.

In another embodiment of this aspect, the cells are stem cells.

In another embodiment of this aspect, the cells are neural stem cells (NSCs).

In another aspect the present invention provides a method of controlling differentiation of stem cells, comprising delivering a nucleic acid into the stem cells using the nucleic acid delivery system according to any embodiments described above.

In one embodiment of this aspect, said stem cells are neural stem cells.

In another embodiment of this aspect, said nucleic acid is a small interfering ribonucleic acid (siRNA).

In another aspect the present invention provides a method of enhancing neuronal differentiation of neural stem cells comprising nanotopography-mediated delivery of siRNA or genes into the neural stem cells using a nucleic acid delivery platform according to any embodiments described above.

In another aspect the present invention provides a gene therapy for treating a disease or disorder, comprising administering to a patient in need thereof stem cells that have undergone controlled differentiation according to the method described above.

In one embodiment of this aspect, the disease or disorder is a neuronal disease or disorder, and the stem cells are neural stem cells that have undergone enhanced neuronal differentiation.

In another aspect, the present invention provides a nucleic acid delivery kit comprising a nucleic acid delivery platform according to any embodiments described above.

In another aspect the present invention provides a method of preparing a nucleic acid delivery platform, comprising the steps of: (1) providing a glass substrate; (2) coating the glass substrate with a thin film of gold; (3) forming self-assembled monolayer(s) (SAMs) of a negatively charged bifunctional organic compound on the gold film; (4) generating a silica nanoparticle (SiNP) film on the coated gold film; and (5) coating the SiNP film with one or more ECM protein(s).

In one embodiment of this aspect, said generating comprises centrifugation of the glass substrate in a solution of positively charged SiNPs.

In another embodiment of this aspect, said negatively charged bifunctional organic compound is a fatty acid having an end thiol (—SH) group.

In another embodiment of this aspect, said fatty acid comprises from about 6 to about 30 carbon atoms.

In another embodiment of this aspect, said fatty acid comprises from about 10 to about 20 carbon atoms.

In a preferred embodiment, said fatty acid is 16-mercaptohexadecanoic acid (MHA).

In another embodiment of this aspect, the ECM proteins are independently selected from the group consisting of laminin, fibronectin, collagen, and combinations thereof.

In a preferred embodiment of this aspect, the ECM protein is laminin.

In another embodiment of this aspect, the sizes of silica nanoparticles are in the range of 50 nm to 700 nm.

In another embodiment of this aspect, the sizes of silica nanoparticles are in the range of 100 nm to 300 nm.

In another embodiment of this aspect, said thin film of gold has a thickness in the range of 5-20 nm.

In another embodiment, the thin film of gold has a thickness in the range of 8-16 nm.

Figure 2:
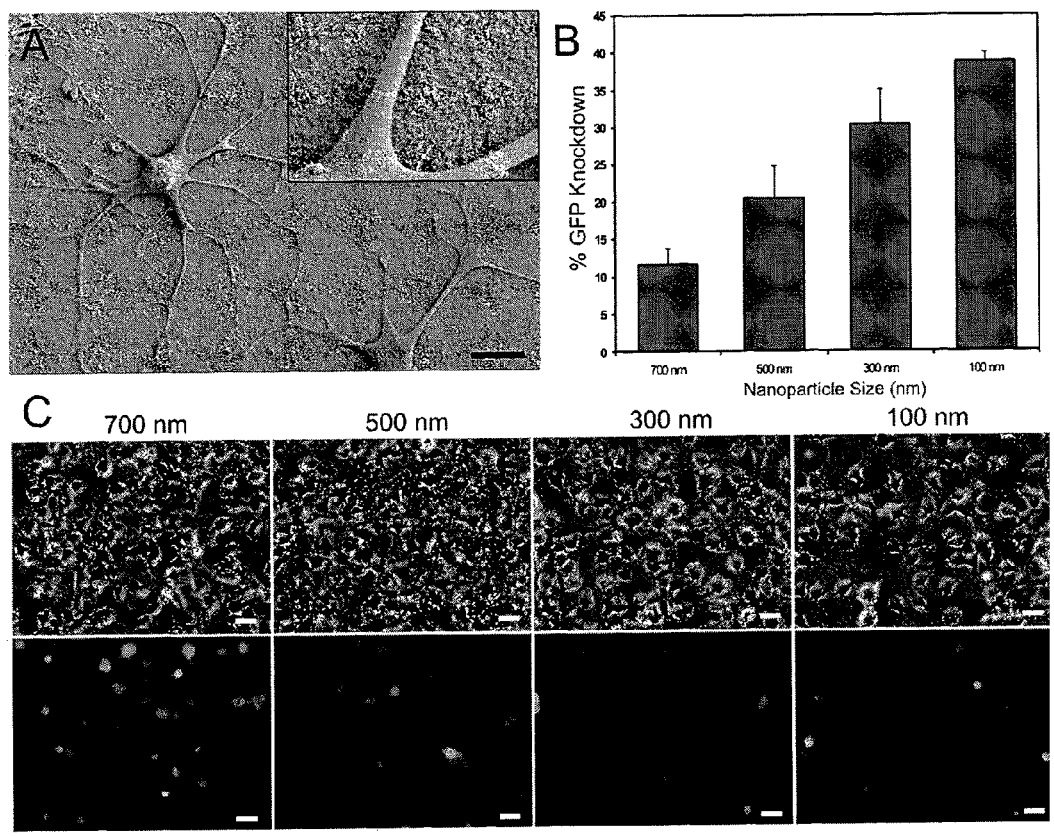
FIG. 2 illustrates size-dependent nanoparticle films for the delivery of GFP siRNA into NSCs. (A) Scanning electron microscopy (SEM) image of NSCs on 100 nm SiNP films. (B) Quantitative comparison of the percentage of GFP knockdown in NSCs on nanoparticle films ranging in size from 100-700 nm. (C) Phase contrast images (top row) and fluorescence images for GFP (bottom row) of cells on nanoparticle films ranging in size from 100-700 nm. Scale bars: 20 μm.
Figure 5:
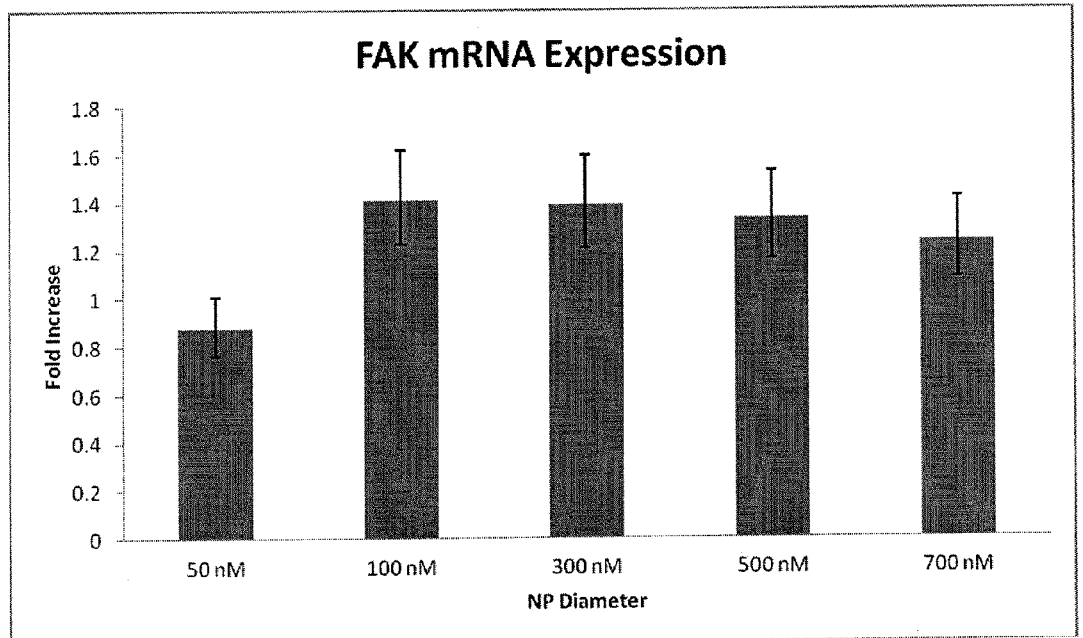
FIG. 5 illustrates quantitative real-time RT-PCR analysis for FAK of NSCs grown on NanoRU containing nanoparticles (SiNP) with sizes ranging from 50-700 nm.

Size of the Nanotopographical Features Determines siRNA-based Gene Knockdown in NSCs We began by investigating the effect of size of the SiNPs on siRNA delivery into the NSCs. We generated films of SiNPs ranging from 50 nm to 700 nm in diameter and coated them with a solution of laminin (10 μg/mL) and siRNA molecules (200 nM) against hmGFP. Laminin is a well-established extracellular matrix protein which binds to the integrin receptors on the surface of the NSCs, and is essential for cell adhesion and growth. The negatively charged laminin and siRNA molecules condensed on the positively charged SiNPs. The NSCs growing on the films were imaged using the fluorescence microscope and the knockdown of hmGFP was quantified after 72 h. We observed a size-dependent knockdown of hmGFP in the NSCs, with the 100 nm SiNPs showing the highest knockdown and the 700 nm particles showing the lowest knockdown (FIGS. 2B and 2C). These results were normalized with the fluorescence from NSCs on control substrates containing no SiNPs. To provide the control substrates with a positive charge, the substrates were functionalized with SAMs of cysteamine and subsequently coated with laminin. The knockdown of hmGFP in NSCs on the 50 nm SiNP films was negligible to the control substrates, indicating that features as small as 50 nm are not effective for delivering siRNA. Since it is established that the cell-surface interactions or the cell-ECM interactions are mediated through integrin signaling (Adler, A. F. and Leong, K. W. *Nano Today* 5, 553-569 (2010)), our results, as well as others (Dalby, M. J., et al., *Eur. J. Cell Bio.* 83, 159-169 (2004); Cavalcanti-Adam, E. A., et al., *Biophys, J.* 92, 2964-2974 (2007)), have demonstrated that the varying topographies (different sizes of SiNPs) are responsible for the binding of laminin to integrin receptors on the NSCs, which in turn might have affected siRNA uptake through the formation and disassembly of focal adhesions. It has been reported that nanostructures having feature sizes less than 70 nm causes less focal adhesions to form (Biggs, M. J. P., et al., *Nanomed.-Nanotechnol.* 6, 619-633 (2010); Shi, F., and Sottile, J. *J. Cell Sci.* 121, 2360-2371 (2008)). This could be a primary reason for the minimal knockdown observed in NSCs growing on the 50 nm SiNP films. This was further confirmed by checking mRNA levels of focal adhesion kinase (FAK) using qPCR, wherein 50 nm SiNP films showed the lowest levels of mRNA as compared to control, and 100 nm SiNP films showed the highest mRNA levels of FAK (FIG. 5). Our results thus demonstrated that siRNA uptake by neural stem cells is indeed dependent on the topographical features of the ECM.

To study the effects of different sized nanotopographical features on the efficiency of siRNA transfection and gene knockdown in the NSCs labeled with GFP, we generated monolayers of silica nanoparticles (SiNPs) ranging from 50 nm to 700 nm in diameter on bare glass substrates by centrifuging the substrates in a solution of positively charged SiNPs (See Methods section for details). NSCs labeled with GFP can be used to investigate siRNA-based silencing efficiency as the suppression of GFP does not affect stem cell behaviors such as growth, proliferation, and differentiation. Depending on the size of the SiNPs used, we refer to these SiNP monolayers as NanoRU50, NanoRU100, NanoRU300 and so on. This size-dependent study is critical because the nanotopographical features of the extracellular microenvironment have been shown to affect the adhesion and growth of stem cells, which in turn can influence the substrate-mediated delivery of genetic materials into stein cells. The NanoRUs were coated with a solution of laminin (10 μg/mL) and siRNA molecules (1 μM) against GFP. Laminin is a well-established extracellular matrix (ECM) protein that binds to the integrin receptors on the surface of the NSCs, and is an essential ECM component for the adhesion, growth, and differentiation of NSCs. Negatively charged siRNA molecules and laminin condensed together on the positively charged SiNPs. After 4 h, the solution was removed and NSCs were then cultured and grown on these NanoRUs (FIG. 2A). After 72 h, the NanoRUs were imaged using a fluorescence microscope and the knock-down GFP in the NSCs was quantified. Interestingly, we observed a size-dependent knockdown of GFP in the NSCs from 100 to 700 nm, with the 100 nm SiNPs showing the highest knockdown and the 700 nm particles showing the lowest knockdown (FIG. 28B). These results were normalized with the fluorescence from NSCs on control substrates having no SiNPs. The control substrates (without the SiNP monolayer) had a positively charged surface, which was prepared by functionalizing glass substrates with self-assembled monolayers (SAMs) of 3-Aminopropyltrimethoxy silane (APTES) and subsequently coating them with the same concentrations of siRNA and laminin. While the best GFP-knockdown results were obtained from NanoRU100 and NanoRU300, we observed that NanoRU500 and NanoRU700, having larger SiNPs, did not provide the optimal nanotopographical cues and thereby were not as effective for siRNA delivery into the NSCs. We believe, as the SiNPs become larger, nanotopographical features do not play a significant role in the reverse uptake. Another interesting result was that the knockdown of GFP in NSCs on NanoRU50 was very similar to the control substrates. Our results are further supported by a recent study, which reported that cells typically cannot interact with ECM nanostructures having feature sizes less than 70 nm due to formation of unstable focal adhesions. Therefore, we believe topographical features generated by SiNPs greater than 50 nm, such as 100 nm and 300 nm, provided the most optimal conditions for efficiently delivering siRNA into the NSCs.

We then investigated the mechanism that is responsible for the influence of the nanotopographical features on the uptake of siRNA by the NSCs. It is well known that the cell-surface interactions or the cell-ECM interactions are mediated through integrin signaling. From our results and previous studies from the literature (Dalby, M. J., et al., *Eur. J. Cell Biol.* 83, 159-169 (2004)), we hypothesized that the varying nanotopographies (different sizes of SiNPs) are responsible for the formation and disassembly of focal adhesions, which in turn might have affected siRNA uptake by the NSCs. This was further confirmed by checking mRNA levels of focal adhesion kinase (FAK) using quantitative polymerase chain reaction (qPCR), where 50 nm SiNP films (NanoRU50) showed the lowest levels of mRNA as compared to control, and 100 nm SiNP films (NanoRU100) showed the highest mRNA levels of FAK (FIG. 5). Our results thus confirmed that siRNA uptake by neural stem cells (NSCs) is indeed dependent on the nanotopographical features of the ECM. Although NanoRU100 gave us the highest GFP knockdown, we used NanoRU300 for most of our subsequent experiments as the NanoRU300 comprised of a very well packed 300 nm SiNP monolayer, which was very reproducible and allowed for easier monitoring of their interaction with NSCs.

NanoRU Delivers Only siRNA into NSCs and Not SiNPs

Figure 3:
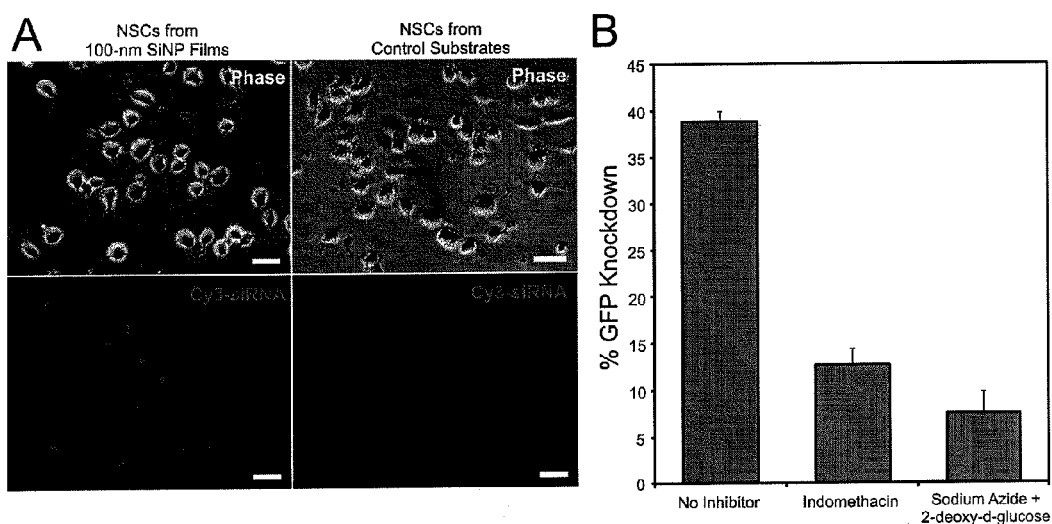
FIG. 3 illustrates proposed mechanisms of siRNA delivery into NSCs. (A) Left column: Phase contrast image and fluorescence image for Cy3 of NSCs grown on 100-nm SiNP films coated with Cy3-labeled siRNA, and then re-attached into a 24-well plate. Right column: Phase image and fluorescence image for Cy3 of NSCs grown on glass covers lips coated with Cy3-labeled siRNA, and then re-attached into a 24-well plate. Scale bars: 20 μm. (B) Quantitative comparison of the percentage of GFP knockdown in the presence of no endocytosis inhibitors, indomethacin and sodium azide plus 2-deoxy-d-glucose.

Another important aspect that needed to be investigated was whether the SiNPs were being taken up along with the siRNAs. To this end, we used NanoRU100 and NanoRU300, wherein the SiNPs were labeled with Alexa-Fluor® 594 dye to generate nanotopographical features on glass substrates. We then deposited siRNA against GFP on the dye-labeled NanoRUs. After 36 h of incubation, the NSCs were detached gently from the NanoRUs using the enzyme Accutase®, and regrown in a 24-well plate. We did not observe any fluorescence (from dye-labeled SiNPs) within the transfected NSCs; however, we observed a clear GFP knockdown due to the siRNA delivered into the NSCs. Similarly, we further confirmed the uptake and localization of siRNA from NanoRU300 using the Silencer® Cy3-labeled negative control siRNA (Ambion), which showed remarkably higher fluorescence compared to the control substrates. This experimental data clearly indicates that the stem cells take up only siRNAs, and not SiNPs. We believe that this is due to the tight packing of the SiNPs within the SiNP monolayer. Additionally, the cohesive forces of attraction between the SiNPs and the substrate may be too strong for the NSCs to break and take up the SiNPs. We believe that this unique feature, where only the siRNA is taken up by the NSCs, makes NanoRU particularly advantageous over conventional transfection methods for stem cell research. To investigate whether the nanoparticles were also being taken up along with the siRNA, we formed films of 100 nm SiNPs labeled with amine reactive Alexa-594 dye along with siRNA against hmGFP. The NSCs were detached gently from the substrates using the enzyme Accutase, and regrown in a 24-well plate. We did not observe any fluorescence in the NSCs; however, we observed a similar hmGFP knockdown in the NSCs as shown in FIG. 2C. To further confirm the uptake of siRNA, we used an siRNA negative control labeled with the Cy3 dye (Ambion). The NSCs were detached and regrown as before and imaged for fluorescence from the Cy3 dye. Bright red fluorescence was observed in the NSCs obtained from the 100 nm SiNP films, which confirmed that only the siRNA was being taken up, which is advantageous since the SiNPs are not introduced within the NSCs and the delivery is purely based upon nanotopography (FIG. 3A). No fluorescence was observed in the NSCs from control substrates (FIG. 3A, having no SiNPs and coated with laminin and Cy3 siRNA).

It was vital for us to investigate the mechanism involved in the uptake of siRNA from NanoRU. ECM proteins such as laminin, fibronectin and collagen pre-adsorbed on surfaces have been previously indicated in enhancing substrate-mediated gene delivery through endocytosis. Gene delivery in such systems depended more upon caveolae- than clathrin-mediated endocytosis. Caveolae-mediated endocytosis is known to be more efficient as it is able to circumvent the degradative lysosomal pathway. To confirm if the dominant endocytic pathway involved in the uptake of siRNA by the NSCs cultured on our NanoRU300 was indeed caveolae-mediated endocytosis, we treated the NSCs with 100 μM of indomethacin (10 min), a specific inhibitor of caveolae-mediated endocytosis. We also treated the NSCs with a mixture of 10 mM sodium azide and 5 mM 2-deoxy-D-glucose (10 min) as this mixture inhibits all endocytotic pathways within the NSCs. After 72 h we observed a 13% knockdown of GFP in NSCs treated with Indomaethacin and a 7% knockdown in NSCs treated with the mixture of sodium azide and 2-deoxy-D-glucose, which was significantly lower than the 40% knockdown observed in untreated NSCs (FIG. 38). We hypothesize that the knockdown we observed in the presence of inhibitors was due to the uptake of siRNA when the cells were left untreated for a brief period of time as they were still attaching to the SiNP films. Collectively, these results imply that the uptake of siRNA using NanoRU relies mainly on the caveolae-mediated endocytosis.

Controlling Neuronal Differentiation of NSCs Using NanoRU

Figure 4:
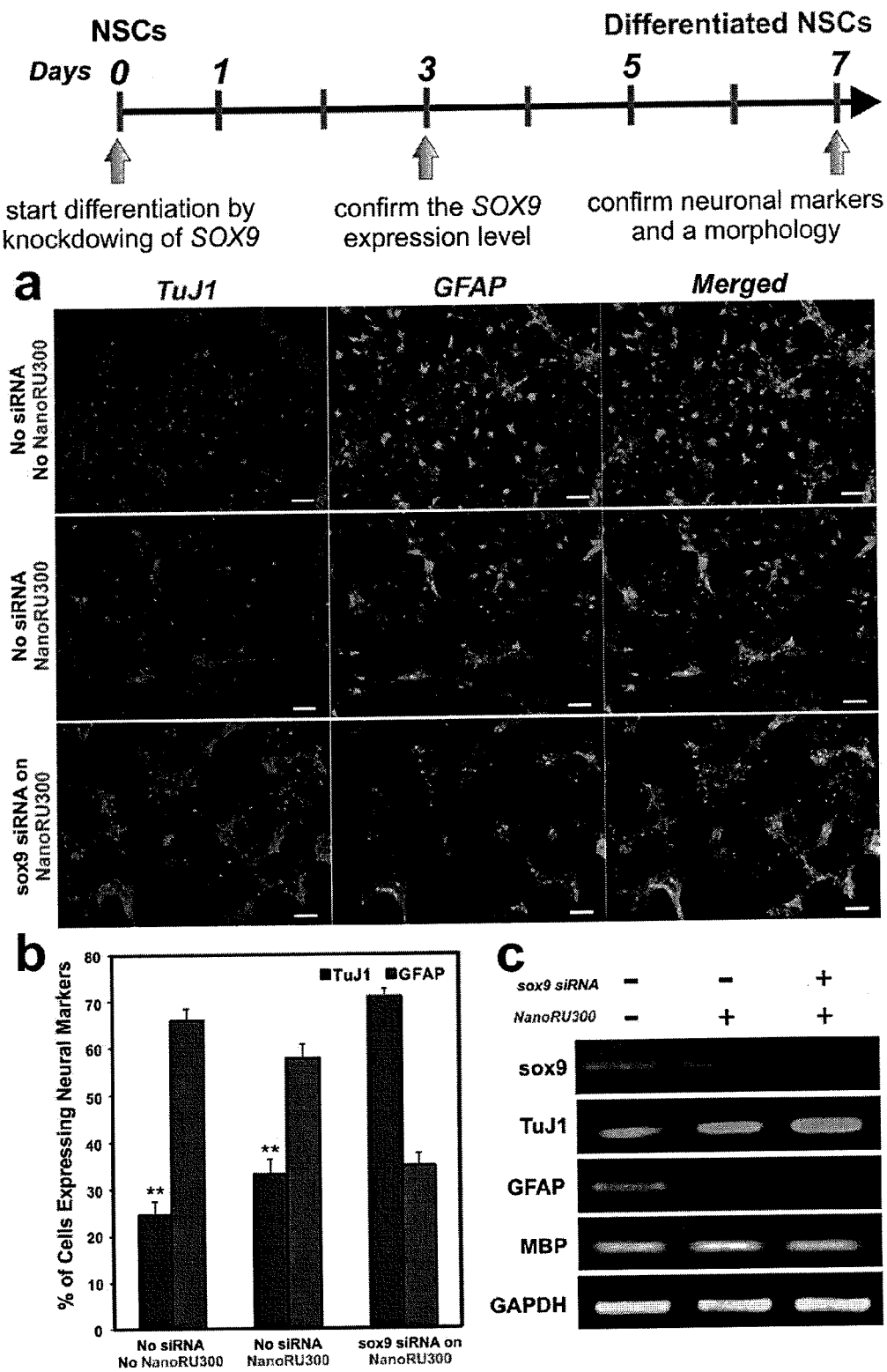
FIG. 4 illustrates NSC differentiation on NanoRU300 coated with SOX siRNA. a, Fluorescence images of cells stained for the nucleus (blue), the neuronal marker TuJ1 (red, left column), the astrocyte marker GFAP (green, middle column) and merged (last column) show the extent of differentiation of NSCs grown on: no NanoRU300 or SOX9 siRNA coating (top row), NanoRU300 without SOX9 siRNA coating (middle row), and NanoRU300 with SOX9 siRNA coating (bottom row). Scale bars: 50 μm. b, Quantitative comparison of the percentage of cells expressing Tuj1 and GFAP. Student's unpaired t-test was used for evaluating the statistical significance for cells stained for Tuj1, compared to the SOX9 siRNA on NanoRU300 condition (**=P<0001), c, RT-PCR analysis reveals differences in transcript levels for SOX9 and differentiation markers for neurons (TuJ1), astrocytes (GFAP) and oligodendrocytes (MBP) in the presence (+) or absence (−) of SOX9 siRNA and/or NanoRU300.
Figure 6:
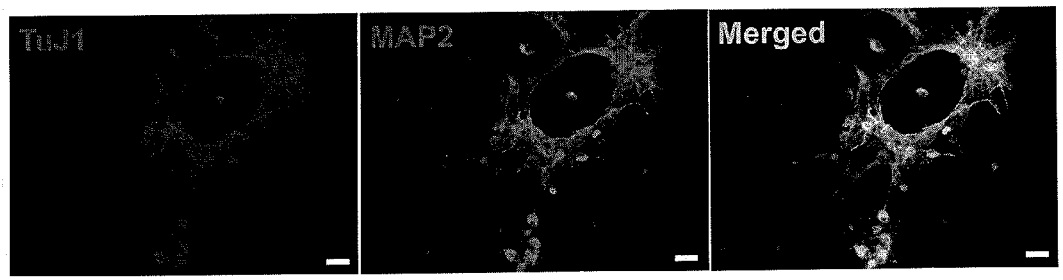
FIG. 6 illustrates fluorescence images of NSCs grown on NanoRU300 films coated with SOX9 siRNA stained for the neuronal markers TuJ1 and MAP2. The merged images shows the co-localization of the two neuronal markers. Scale bars: 20 μm.

Having demonstrated the efficiency of NanoRU by delivering siRNA against GFP, we focused on using NanoRU to enhance the neuronal differentiation of NSCs by suppressing the expression of a specific protein or gene. We used NanoRU to deliver siRNA against SOX9 (siSOX9), a well-established transcription factor which acts as a switch between neuronal and glial differentiation When SOX9 is "turned on," a higher percentage of NSCs differentiate into astrocytes (glial cells), and when "turned off," a higher percentage of NSCs differentiate into neurons. Specifically, we used NanoRU300 to "turn off" SOX9 by coating NanoRU with laminin and siSOX9 following the experimental protocols we had established for knocking down GFP (FIG.). The NSCs were then cultured on the NanoRU300. After 72 h, the knockdown of SOX9Y was analyzed using RT-PCR and a significant decrease in the mRNA levels of SOX9 was observed (FIG. 4C). The NSCs were grown and differentiated on the NanoRU300 coated with the siSOX9 for 7 days. We then used RT-PCR to confirm the increase in the expression of neuronal markers and decrease in the expression of glial markers (FIG. 4C). A remarkable decrease in the expression of the glial marker, glial fibrillary acidic protein (GFAP), and an increase in the expression of the neuronal marker, β-III tubulin (TuJ1), was observed. No significant change was found in the expression of the of oligodendrocyte marker, myelin-binding protein (MBP). We further confirmed and quantified our results by immunostaining for neuronal and astrocyte markers (FIG. 4B). As compared to control substrates (substrates having no SiNPs), a remarkably high percentage of NSCs differentiated into neurons on NanoRU300 coated with siSOX9 (FIG. 4B). As expected, the number of astrocytes considerably decreased when SOX9 was knocked down. Neuronal differentiation was further confirmed by studying the co-localization of two different neuronal markers, TuJ1 and microtubule-associated protein 2 (MAP2) (FIG. 6).

NanoRU for Delivering siRNA into Other Mammalian Cells and miRNA into NSCs

Figure 8:
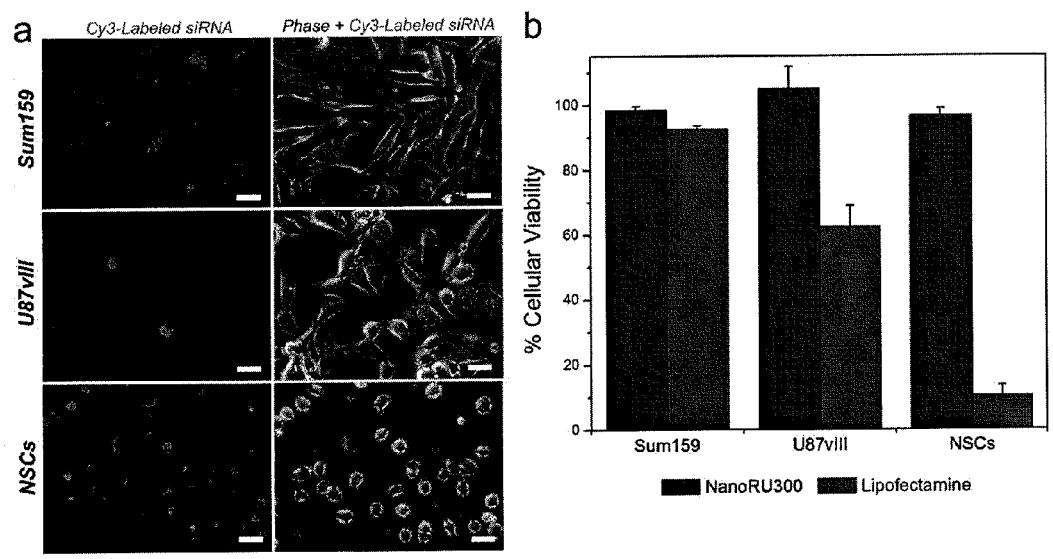
FIG. 8 illustrates cellular uptake of siRNA and cellular viability in different cell types. a, Fluorescence (left column) and merged phase images (right column) of the Silencer® Cy3-labeled negative control siRNA from NanoRU300 in three cell lines: Sum159 (breast cancer cells), U87vIII (brain cancer cells) and rat NSCs (neural stem cells). Scale bars: 20 μm. b, MTS cellular viability of Sum159, U87vIII and NSCs grown on NanoRU300.
Figure 9:
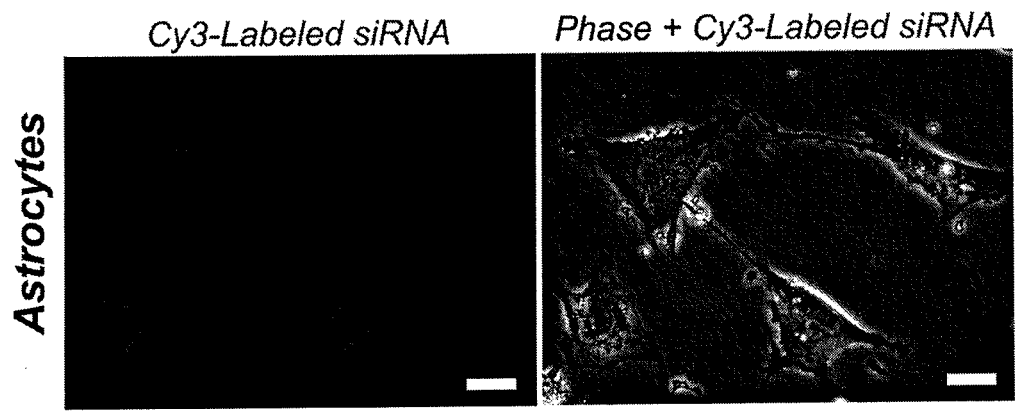
FIG. 9 illustrates fluorescence and phase images depicting the cellular uptake of Silencer® negative control Cy3-labeled siRNA into human astrocytes. Scale bars: 20 μm.
Figure 10:
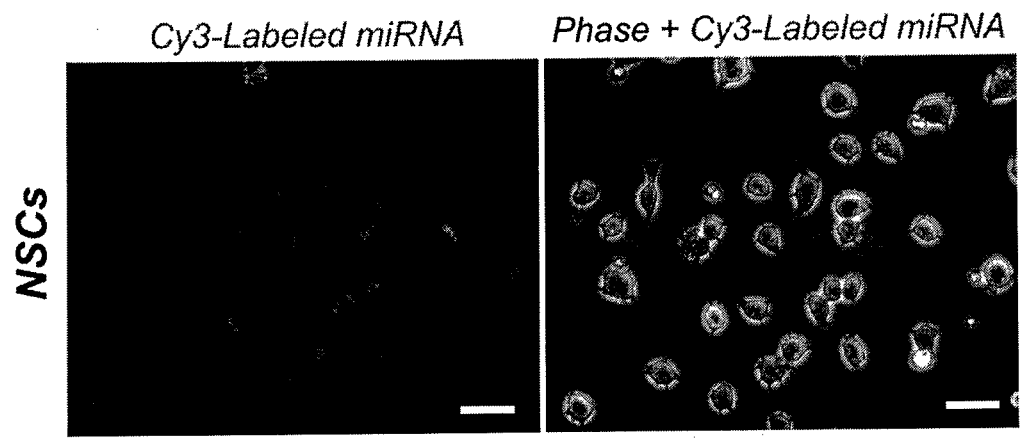
FIG. 10 illustrates fluorescence and phase images depicting the cellular uptake of Cy3-labeled miRNA (pseudocolored green) into rat neural stem cells. Scale bars: 20 μm.

After successfully demonstrating the proficiency of NanoRU for delivering siRNA into stem cells, it was important for us to establish NanoRU as a general platform for delivering siRNA into various other cell lines, thus demonstrating the flexibility of this technology. NanoRU300 was used to deliver Silencer® Cy3-labeled negative control siRNA into other mammalian cells such as astrocytes, brain cancer cells (U87-VIII), and breast cancer cells (SUM159). As these cell lines were adherent, no ECM proteins were required for cell attachment. The cells were detached from NanoRU300 after 36 h, replated in 24 well plates, and then imaged for siRNA uptake (FIG. 8a and FIG. 9). The majority of the cells had taken up the siRNA from NanoRU300, indicating that our technique is efficient and applicable to normal cells, cancer cells, as well as stem cells. Additionally, NanoRU can be easily extended to deliver miRNA, consisting of a larger number of nucleotide base pairs. We successfully delivered the Cy3-dye labeled Pre-miR® negative control (Ambion) using the same protocol that we used for delivering siRNA. The NSCs cultured on NanoRU 300 coated with laminin and miRNA took up the miRNA in a highly efficient manner (FIG. 10).

NanoRU does not Damage Cell Membranes and is Non-toxic

Figure 11:
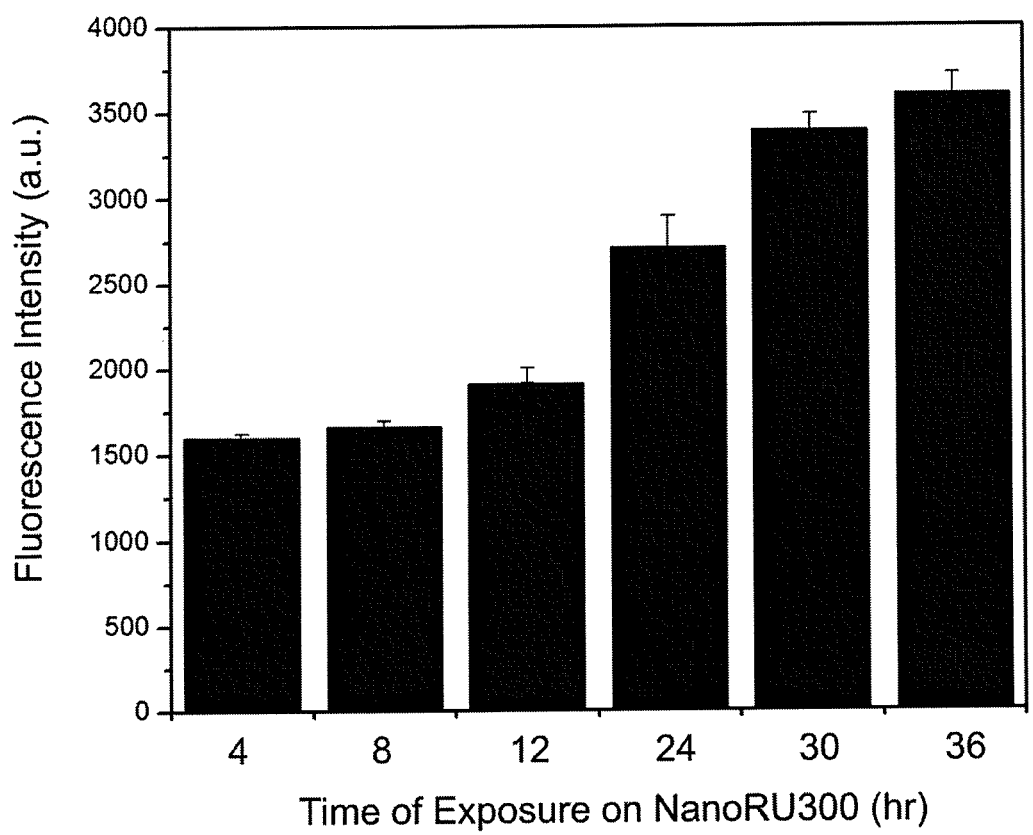
FIG. 11 illustrates time-dependent uptake of Silencer® negative control Cy3-labeled siRNA into rat neural stem cells.

One of the biggest advantages of NanoRU is its biocompatibility and the fact that the transfection begins as soon as the cells are cultured on NanoRU, with the highest transfection observed at 36 h (FIG. 11). On the other hand, most standard solution-mediated transfection protocols using cationic lipids and polymers require a wait period of at least 24 h before the cells can be transfected in order to minimize their toxicity. In addition, the serum proteins in the culture media are known to decrease the transfection efficiency due to the non-specific interaction of serum proteins with the delivery constructs. We compared the cytotoxicity of NanoRU300 with a well-established lipid-based cationic transfection agent, Lipofectamine 2000® (Life Technologies) using the negative control siRNA in three different cell lines, SUM159, U87 VIII and NSCs. The cytotoxic results were analyzed using a standard cell proliferation assay (MTS assay). Interestingly, we found that Lipofectamine 2000®, while less toxic towards cancer cells, was extremely cytotoxic (using manufacturer's recommended transfection condition) towards NSCs, which led to the inhibition of proliferation of 95% of the NSCs within 48 h of being transfected with the negative control siRNA (Ambion) (FIG. 8b). NanoRU300, on the other hand, was shown to be biocompatible with minimal decrease in cell proliferation for all the cell lines tested. Moreover, we believe NanoRU does not cause any physical damage to the cell membranes as the NSCs showed good viability and enhanced neuronal differentiation on NanoRU after an extensive period of 7 days. Furthermore, we believe the nanotopographical features promoted the interactions of genetic materials with the target cells which was evident by the increased formation of focal adhesions. Hence, NanoRU can be especially useful for controlling NSC differentiation, a process which requires the NSCs to survive for more than 7 days in vitro.

Figure 7:
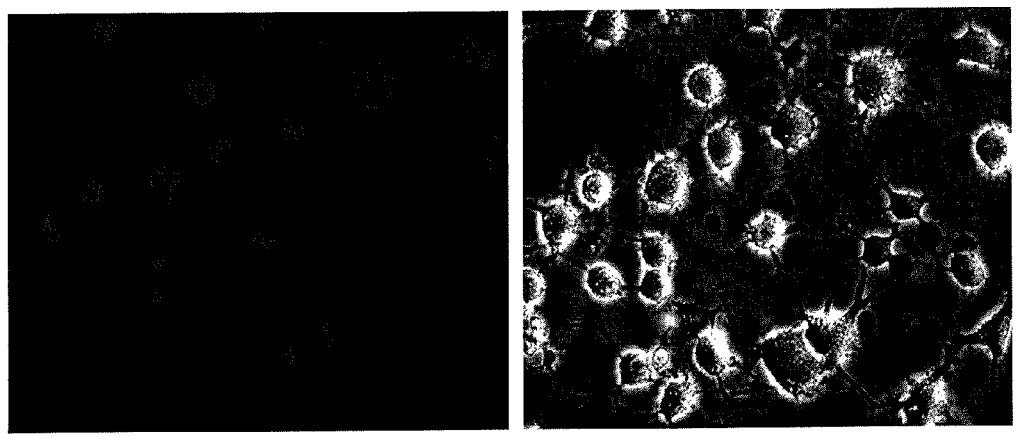
FIG. 7 illustrates expression of DsRed plasmid in NSCs seeded on 100-nm SiNPs coated with the DsRed plasmids.

In summary, we have developed an ECM-based nanotechnology platform for controlling gene expression within neural stem cells using a simple technique to deliver siRNA. We demonstrate the successful delivery of siRNA against SOX9 to significantly enhance the neuronal differentiation of the NSCs. The presence of laminin in the microenvironment greatly enhances the siRNA delivery through caveolae-mediated endocytosis. In addition, this platform completely relies on the cells' ability to sense the nanotopographical features and take up only the siRNA from its microenvironment and does not require the use of cationic polymers, viruses, or nanowires which may impale and perturb the cells. The technique is not limited to the size of nucleic acids and can also be used to deliver plasmid DNA into neural stem cells. We coated 100 mm SiNP films with plasmid DNA for DsRed and after 24 h, most of the cells on the 100 nm SiNP films expressed the DsRed protein (FIG. 7). Furthermore, the platform may be extended by making patterns of SiNPs having varying geometries and dimensions to control the cell-cell and cell-ECM interactions as well as deliver siRNA to synergistically enhance neuronal differentiation.

The NanoRU of the present invention is a novel nanotopography-mediated reverse uptake platform for the genetic manipulation of NSCs in a highly effective manner. This platform was employed to control the neuronal differentiation of stem cells by using nanotopographical features to deliver siRNAs inside cells. Although NanoRU can be successfully applied to deliver siRNA into various cell lines, one of the main reasons for focusing on NSCs as a model cell line was to establish its biocompatibility and ease of application for stem cells, which are much more sensitive to the cytotoxic exogenous materials typically used for siRNA delivery. We used NanoRU not only to deliver siRNA into NSCs but also to ensure the survival and differentiation of the transfected NSCs for a long period of time. Furthermore, we believe NanoRU and its application can significantly complement recent advances in research efforts to control stem cell differentiation based on physical cues such as patterns and bioactive scaffolds of ECM materials. Even though we have only explored proof-of-concept experiments involving genetic manipulation and differentiation of NSCs, we expect that NanoRU can be extended, with straightforward modifications of the aforementioned protocols, to a wide range of nanomaterials and biomolecules (e.g. miRNA, proteins, and small molecules). Finally, we believe NanoRU is a valuable platform which will complement conventional genetic manipulation tools in cell biology. For example, one of the key aspects behind stem cell-based therapies for many devastating diseases is to transplant stem cells or differentiated stem cells at the site of injury, after genetically manipulating them. The exogenous delivery vehicles used for siRNA delivery would be present within the stem cells and could trigger a strong immune response or tumor formation after stem cell transplantation. Therefore, our NanoRU-based siRNA delivery might help overcome one of the critical barriers in stem cell-based tissue engineering.

Overall, while the application of the delivery platform was demonstrated using a specific cell line (i.e. NSCs), ECM protein (i.e. laminin) and siRNA sequence (i.e. SOX9), this platform can easily be used applied for any desirable combination of other stem cell lines, ECM proteins and nucleic acids.

In this application all terms unless otherwise defined take the ordinary meaning known to a person of ordinary skill in the art. The following non-limiting examples serve to further illustrate the present invention.

EXAMPLES

Methods

Generating Nanoparticle Films

Polycrystalline Au films were prepared by thermally depositing ~5-6 nm thick Ti layer followed by ~10-20 nm Au deposition on cover glass substrates (Fisher No. 1) under a high vacuum condition (base pressure ~$5 \times 10^{-6}$ torr). For generating films of nanotopographical features, silicon oxide nanoparticles (SiNPs, Corpuscular Inc) of different sizes were utilized. The gold-coated cover slips were first functionalized with self-assembled monolayers (SAMs) of negatively charged 16-mercaptohexadecanoic acid (MHA, Sigma) using microcontact printing. Flat PDMS stamps were inked with 5 mM ethanolic solution of MHA and the Au-coated substrates were stamped for 5 s. The substrates were then washed with ethanol and dried under a nitrogen stream. Alternatively, the substrates could also be functionalized by simply incubating in 5 mM ethanolic solution of MHA overnight. The substrates were then centrifuged at 1000 RPM for 1 min in a 2 mL eppendorf tubes containing 25 mg/mL of the positively charged (amine terminated) SiNP solution. The sizes used were 50 nm, 100 nm, 300 nm, 500 nm and 700 nm. The substrates were then washed with distilled water and dried under nitrogen.

NanoRU Preparation

Cover glass (Number 1, 22 mm×22 mm; VWR) was cut equally into smaller pieces (18 mm×6 mm) and sonicated in Nanopure water (18.2 mOhm) for 10 mins and then cleaned in piranha solution (a 3:1 mixture of sulphuric acid and hydrogen peroxide) for 10 main (Caution: Piranha solution is extremely corrosive). The glass coverslips were then washed again in Nanopure water (18.2 Mohm) and dried under a stream of pure nitrogen. To generate films of nanotopographical features, silicon oxide nanoparticles (SiNPs, Corpuscular Inc) of different sizes were utilized. The washed cover slips were centrifuged at 2000 RPM for 2 min in a 2 mL eppendorf tube containing 25 mg/mL, of the positively charged (amine terminated) SiNP solution. The sizes used were 50 nm, 100 nm, 300 am, 500 nm and 700 nm. The substrates were then washed with Nanopure water and dried under a stream of pure nitrogen. For functionalization with (3-aminopropyl)triethoxysilane (APTES), the washed glass cover slips were left in a beaker containing 1% APTES solution in pure ethanol for 2 h. The cover slips were then rinsed thoroughly with ethanol and dried under nitrogen. They were then baked at 100° C. in an oven for 10 min.

Coating SiNP Films with Laminin and siRNA

The positively charged films (NanoRUs) were then coated with siRNA and laminin, both of which are negatively charged in phosphate buffer saline (PBS, pH 7.4; Life Technologies). In a culture hood, the films (NanoRUs) were coated with a 10 µg/mL solution of laminin containing 100 pmoles of the desired siRNA (against GFP or SOX9). The GFP siRNA sequence was: Antisense—5'-CCAACGACAUCAGCGAC-UAUU-3' (SEQ ID NO 1), Sense—3'-UUGGUUGCU-GUAGUCGCUGAU-5' (SEQ ID NO 2). The SOX9 siRNA sequence was Antisense—5'-AACGAGAGCGAGAA-GAGACCC-3' (SEQ ID NO 3), Sense—3'-UUGCU-CUCGCUCUUCUCUGGG-5' (SEQ ID NO 4). The solution was left on top of the SiNP films (NanoRUs) for 3 h, and then simply removed by dipping the films once in sterile phosphate buffer saline, pH 7.4 (PBS). The negatively charged laminin and siRNA molecules simply condense on the positively charged SiNP films (NanoRUs). The coated films (NanoRUs) were then put into 12-well plates and 1 mL suspensions of NSCs were seeded with density of $1.25 \times 10^5$ NSCs/ml of Millitrace media (Millipore) in the absence of growth factors such as basic fibroblast growth factor (bFGF). The NSCs were maintained in a humidified atmosphere at 37° C. and 5% $CO_2$. After 12 h, the films were transferred to new well plates to prevent non-specific attachment of the floating NSCs. The media was then changed every other day until Day 7. On Day 7, the cells were either fixed for immunocytochemistry or lysed for PCR analysis.

Rat Neural Stem Cell (NSC) Culture and Differentiation

Rat neural stem cell line (Millipore) was purchased and routinely expanded according to the manufacture's protocol. The NSCs were maintained in laminin (Sigma, 20 µg/ml) coated culture dishes precoated with poly-L-lysine (10 µg/ml) in Millitrace media (Millipore) supplemented with antibiotics, penicillin and streptomycin (Life Technologies), in the presence of basic fibroblast growth factor (bFGF-2, 20 ng/ml, Millipore). All of the cells were maintained at 37° C. in a humidified atmosphere of 5% $CO_2$. For consistency, the experiments were carried out on the cells between passages 2 and 5. Neural differentiation was initiated by changing the medium to basal medium (without bFGF-2) on the SiNP films (NanoRUs) coated with laminin and siRNA. The cells were allowed to differentiate for 7 days with the basal medium in each being exchanged every other day.

Culturing U87-EGFRvIII, SUM159, and Astrocytes

For each of the cell lines, experiments were carried out on cells between passages 2 and 10. The NanoRU300, coated with Silencer Cy+3-labeled negative control siRNA, were put into wells of a 12 well plate and each well containing the substrate was seeded with 80,000 cells. After 24 h, the substrates were moved into a new 12 well plate.

| Cell Line | Media Components |
|---|---|
| U87-EGFRvIII | DMEM (Dulbecco's modified Eagle's medium) with high glucose (Invitrogen), 10% Fetal Bovine Serum (FBS), 1% streptomycin-penicillin, 1% glutamax (Invitrogen), and the selection marker, hygromycin B (30 µg/ml) |
| SUM159 | Ham's F12 with insulin (5.0 µg/mL), hydrocortisone (1.0 µg/mL), 10 mM HEPES buffer, 5% Fetal Bovine Serum (FBS), 1% streptomycin-penicillin |
| Astrocytes | DMEM with high glucose (Invitrogen), 10% Fetal Bovine Serum (FBS), 1% streptomycin-penicillin, 1% glutamax (Invitrogen) |

Cell Viability Assays

Cell viability of the above cell lines on NanoRU300 was compared with Lipofectamine 2000® (Life Technologies) for delivering Silencer® negative control siRNA (Ambion). The percentage of viable cells was determined by MTS assay following standard protocols described by the manufacturer. All experiments were conducted in triplicate and averaged. The quantification of cytotoxicity was done using MTS assay after incubating cells in the presence of the manufacturer's recommended concentration, of Lipofectamine 2000®. The data is represented as formazan absorbance at 490 nm, considering the control (untreated) cells as 100% viable.

at 4° C. in solutions of primary antibodies in PBS containing 10% NGS. After washing three times with PBS, the samples were incubated for 1 h at room temperature in solution of anti-mouse secondary antibody labeled with Alexa-Fluor® 647 and anti-rabbit secondary antibody labeled with Alexa-Fluor® 546 (1:200, Life Technologies). Hoechst 33342 (1:500, Life Technologies) in PBS containing 10% NGS to observe neuronal and glial, differentiation. After washing the samples thrice with PBS the substrates were mounted on glass slides using ProLong® Gold antifade (Life Technologies) to minimize quenching by gold. The mounted samples were imaged using Nikon TE2000 Fluorescence Microscope, ImageJ (NIH) was used for comparative analysis and quantifying the cells expression TuJ1 and GFAP.

PCR Analysis

Total RNA was extracted using Trizol. Reagent (Life Technologies) and the mRNA expression level of FAK, GFAP, MBP, SOX9 and TUJ1 were analyzed using Reverse Transcriptase PCR (RT-PCR) and quantitative PCR (qPCR). Specifically, cDNA was generated from 1 µg of total RNA using the Superscript III First-Strand Synthesis System (Life Technologies). Analysis of mRNA was then accomplished using primers specific to each of the target mRNAs, RT-PCR reactions were performed in a Mastercycler Ep gradient S (Eppendorf) and images were captured using a Gel Logic 112 (Carestream) imaging system. qPCR reactions were performed using SYBR Green PCR Master Mix (Applied Biosystems) in a StepOnePlus Real-Time PCR System (Applied Biosystems) and the resulting Ct values were normalized to Gapdh. Standard cycling conditions were used for all reactions with a melting temperature of 60° C. Primers are listed below:

| Gene | F Primer | R Primer | Size (pp) |
|---|---|---|---|
| FAK | 5'-CAATGCCTCCAAATTGTCCT-3' (SEQ ID NO 5) | 5'-TCCATCCTCATCCGTTCTTC-3' (SEQ ID NO 6) | 157 |
| GAPDH | 5'-ATGACTCTACCCACGGCAAG-3' (SEQ ID NO 7) | 5'-GGAAGATGGTGATGGGTTTC-3' (SEQ ID NO 8) | 87 |
| GFAP | 5'-GAGAGAGATTCGCACTCAGTA-3' (SEQ ID NO 9) | 5'-TGAGGTCTGCAAACTTGGAC-3' (SEQ ID NO 10) | 89 |
| MBP | 5'-CACAAGAACTACCCACTACGG-3' (SEQ ID NO 11) | 5'-GGGTGTACGAGGTGTCACAA-3' (SEQ ID NO 12) | 103 |
| Sox9 | 5'-AGGAAGCTGGCAGACCAGTACC-3' (SEQ ID NO 13) | 5'-TCTCTTCTCGCTCTCGTTCA-3' (SEQ ID NO 14) | 96 |
| TUJ1 | 5'-ACTTTATCTTCGGTCAGAGTG-3' (SEQ ID NO 15) | 5'-CTCACGACATCCAGGACTGA-3' (SEQ ID NO 16) | 97 |

Immunocytochemistry

To investigate the extent of neuronal differentiation, at Day 6, the basal medium was removed and the cells fixed for 15 minutes in Formalin solution (Sigma) followed by two PBS washes. Cells were permeabilized with 0.1% Triton X-100 in PBS for 10 minutes and non-specific binding was blocked with 5% normal goat serum (NGS, Life Technolocies) in PBS for 1 hour at room temperature. To study the extent of neuronal differentiation the primary mouse antibody against TuJ1 (1:500, Covance) and primary rabbit antibody against MAP2 (1:100, Cell Signaling) was used and for glial differentiation the primary rabbit antibody against GFAP (1:300, Dako) was used. The fixed samples were incubated overnight The foregoing examples and description of the preferred embodiments should be taken as illustrating rather than as limiting the present invention as defined by the claims. As will be readily appreciated by those skilled in the art, numerous variations and combinations of the features set forth above can be utilized without departing from the present invention as set forth in the claims. Such variations are not regarded as a departure from the spirit and script of the invention, and all such variations are intended to be included within the scope of the following claims. All references cited hereby are incorporated by reference in their entirety.

The invention claimed is:

1. A nucleic acid delivery system comprising at least one nucleic acid, a self-assembled silicon oxide (silica) nanoparticle (SiNP) monolayer, and a film comprising one or more of extracellular matrix (ECM) proteins, wherein the silicon oxide nanoparticle monolayer is coated with the film, wherein:
  the film has topographical features capable of facilitating delivery of the at least one nucleic acid into cells;
  the topographical features enable cellular uptake of the at least one nucleic acid without cellular uptake of the silicon oxide nanoparticle monolayer; and
  the sizes of silica nanoparticles are in the range of 50 nm to 700 nm.

2. The nucleic acid delivery system of claim 1, wherein said silica nanoparticles (SiNPs) are assembled on a thin film of gold coated with a self-assembled monolayer (SAM) of a bifunctional organic compound.

3. The nucleic acid delivery system of claim 2, wherein said bifunctional organic compound comprises a thiol (—SH) end group and a carboxylic acid (—COOH) end group.

4. The nucleic acid delivery system of claim 1, wherein said one or more ECM proteins are independently selected from the group consisting of laminin, fibronectin, collagen, and combinations thereof.

5. The nucleic acid delivery system of claim 1, wherein said ECM protein is laminin.

6. The nucleic acid delivery system of claim 1, wherein the sizes of silica nanoparticles are in the range of 100 nm to 300 nm.

7. The nucleic acid delivery system of claim 1, wherein said nucleic acid is a small interfering ribonucleic acid (siRNA).

8. The nucleic acid delivery system of claim 1, wherein said cells are mammalian cells.

9. The nucleic acid delivery system of claim 1, wherein said cells are astrocytes or cancer cells.

10. The nucleic acid delivery system of claim 1, wherein said cells are stem cells.

11. The nucleic acid delivery system of claim 1, wherein said cells are neural stem cells (NSCs).

12. A nucleic acid delivery kit comprising a nucleic acid delivery platform of claim 1.

* * * * *

UNITED STATES PATENT AND TRADEMARK OFFICE
CERTIFICATE OF CORRECTION

PATENT NO. : 9,114,092 B2
APPLICATION NO. : 13/751690
DATED : August 25, 2015
INVENTOR(S) : Lee et al.

It is certified that error appears in the above-identified patent and that said Letters Patent is hereby corrected as shown below:

In the Specification

At Column 1, Line 16, delete:
"The invention described herein was supported in whole or in part by grants from the National Institutes of Health (New Innovator Award No. NIH-IDP20D00646201). The U.S. Government has certain rights in this invention."

And insert:
--This invention was made with government support under grant number OD006462 awarded by the National Institutes of Health. The government has certain rights in the invention.--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*